US00PP08203P

United States Patent [19]

VandenBerg

[11] Patent Number: Plant 8,203

[45] Date of Patent: Apr. 13, 1993

[54] CHRYSANTHEMUM PLANT NAMED LIGHT FALMA

[75] Inventor: Cornelis P. VandenBerg, Salinas, Calif.

[73] Assignee: Yoder Brothers, Inc., Barberton, Ohio

[21] Appl. No.: 756,837

[22] Filed: Sep. 9, 1991

[51] Int. Cl.[5] ..... A01H 5/00

[52] U.S. Cl. ..... Plt./79

[58] Field of Search ..... Plt./76, 79

[56] References Cited

U.S. PATENT DOCUMENTS

P.P. 5,326 11/1984 Meek, deceased et al. ..... Plt. 79
P.P. 5,996 5/1987 Duffett ..... Plt. 79
4,616,099 10/1986 Sparkes ..... 47/58

OTHER PUBLICATIONS

Chan, 1966, "Chrysanthemum and rose mutations induced by X-rays", Am. Soc. Hort. Sci. Proc., pp. 613-620.

Broertjes, 1966, "Mutation breeding of Chrysanthemums", Euphytica, 15:156-162.

Dowrick et al., 1966, "The induction of mutations in Chrysanthemum using X- and gamma radiation", Euphytica, 15:204-210.

Gosling, ed., 1979, "The Chrysanthemum Manual-6th edition", The National Chrysanthemum Society, London, Essex Telegraph Press, Ltd., pp. 329-336.

Broertjes, et al., 1978, "Application of Mutatiton Breeding Methods in the Improvement of Vegetatively Propagated Crops", Elsevier Sci. Pub. Co., New York, pp. 162-175.

Broertjes, et al., 1980, "A mutant of a mutant of a . . . Irradiation of progressive radiation-induced mutants in a mutation breeding programme with *C. morifolium*", Euphytica, 29:526-530.

Searle, et al., 1968, "Chrysanthemums the Year Round", Blanford Press, London, pp. 27-29, 320-327.

*Primary Examiner*—Howard J. Locker
*Attorney, Agent, or Firm*—Foley & Lardner

[57] ABSTRACT

A Chrysanthemum plant named Light Falma particularly characterized by its flat capitulum form; decorative capitulum type; light-orange ray floret color; diameter across face of capitulum of 60 to 70 mm when fully opened, when grown as single stem cut mum; photoperiodic flowering response of 65 to 68 days to short days in Bogota, Colombia, under temperatures of minimum 6.3 degrees Celsius night and maximum 29 degrees Celsius day; plant height, with 14 long days prior to start of short days, ranges from 102 to 117 cm; peduncle length of the first lateral at flowering after removing the apical bud ranges from 8 to 10 cm; peduncle length of the fourth lateral ranges from 13 to 20 cm; and excellent tolerance to low night temperatures for bud initiation and flower development.

1 Drawing Sheet

The present invention comprises a new and distinct cultivar of Chrysanthemum, botanically known as *Dendranthema grandiflora*, and referred to by the cultivar name Light Falma.

Light Falma, idenified as 3297 (81-795D30), is a product of a mutation induction program. The new cultivar was discovered and selected by Cornelis P. VandenBerg in September, 1988, in a controlled environment in Salinas, Calif., as one flowering plant within a flowering block established as rooted cuttings from stock plants which had been exposed as unrooted cuttings to an X-ray source of 1500 rads in Fort Myers, Fla., in March, 1988. The irradiated parent cultivar was the cultivar identified as Falma, disclosed in U.S. Plant Pat. No. 5,996, and described as a cut spray mum with a flat capitulum form; a decorative capitulum type; an orange-bronze ray floret color; a diameter of capitulum of 60 to 70 mm when fully open; a flowering response time of 49 to 58 days to short days when grown in Salinas, Calif. and of 63 to 68 days when grown in Bogota, Colombia; a plant height of 89 to 104 cm when grown with 6 to 8 long days prior to start of short days in Salinas, Calif., and of 102 to 120 cm when grown with 14 to 15 long days prior to start of short days in Bogota, Colombia; and excellent tolerance to low night temperatures for bud initiation and flower development as shown in repeated testing in Bogota, Colombia, with average low night temperatures of 6.3 to 10 degrees Celsius inside the greenhouse. The description of the parent Falma is based on flowering over many years in California and in Colombia, and has a wider range of characteristics than disclosed in the Plant Patent for Falma, for which the descriptions of characteristics were based on considerably less flowerings.

The irradiation program resulting in Light Falma had as its primary objective the expansion of color ranges of the parent cultivar Falma. The irradiation program comprised irradiating cuttings of the parent cultivar at irradiation levels of 1500, 1750 and 2000 rads. A total of 1,202 cuttings harvested from a total of 225 irradiated plants were planted on Aug. 8, Jul. 25, and Jul. 18, 1988, respectively. Of these, 8 initial selections were made, which selections were then revegetated and reflowered. Three consecutive flowerings in Salinas, Calif., resulted in discarding 4 of the original 8 selections on Jun. 15, 1989. The 4 remaining selections were repeatedly tested in Bogota, Colombia. These tests resulted in discarding 2 of the 4 remaining selections on Apr. 10, 1990. Of the 2 remaining selections, 3297 (81-795D30) was finally selected and identified as Light Falma, and 3212 (81-795B30) was finally selected and designated as Dark Falma. A plant patent application in the name of applicant for Dark Falma is pending.

The first act of asexual reproduction of Light Falma was accomplished when vegetative cuttings were taken from the initial selection in November, 1988, in a controlled environment in Salinas, Calif., by technicians working under supervision of Cornelis P. VandenBerg.

Horticultural examination of controlled flowerings of successive plantings has shown that the unique combination of characteristics as herein disclosed for Light Falma are firmly fixed and are retained through successive generations of asexual reproduction.

Light Falma has not been observed under all possible environmental conditions. The phenotype may vary with variations in environment such as temperature, light intensity and daylength, without, however, any variance in the genotype.

The following observations, measurements and comparisons describe plants grown in Bogota, Colombia, under greenhouse conditions which approximate those generally used in commercial greenhouse practice. The low night temperature tolerance was determined in repeated flowerings in Bogota, Colombia, with an average minimum low night temperature inside the greenhouse during our trials ranging from 6.3 to 10.0 degrees Celsius. Because of the importance of the parent cultivar Falma in Colombia, more extensive testing was carried out in Colombia than in California, and the traits listed below are based on the flowering trials in Bogota, Colombia.

The following traits have been repeatedly observed and are determined to be basic characteristics of Light Falma, which, in combination, distinguish this Chrysanthemum as a new and distinct cultivar:

1. Flat capitulum form.
2. Decorative capitulum type.
3. Light-orange ray floret color.
4. Diameter across face of capitulum of 60 to 70 mm when fully opened, when grown as a single stem cut mum.
5. Photoperiodic flowering response of 65 to 68 short days in Bogota, Colombia, under temperatures of minimum 6.3 degrees Celsius night and maximum 29 degrees Celsius day.
6. Plant height, with 14 long days prior to start of short days, ranges from 102 to 117 cm.
7. Peduncle length of the first lateral at flowering after removing the apical bud ranges from 8 to 10 cm; peduncle length of the fourth lateral ranges from 13 to 20 cm.
8. Excellent tolerance to low night temperatures for bud initiation and flower development.

The accompanying color photographic drawing is a view of a single stem of Light Falma, with the colors being as nearly true as possible with illustrations of this type. Of the commercial cultivars known to the inventor, the most similar in comparison to Light Falma is the parent cultivar Falma. In most flowering trials all traits of Light Falma are similar to those of Falma, except for the ray floret color. The ray floret of color of Light Falma is a significantly lighter orange-bronze than the ray floret color of Falma. In one of our trials in Bogota, Colombia, Light Falma was 2.5 to 5 cm taller than Falma, and 2 to 3 days slower in flowering response when compared with Falma, growing side by side. Also, at flowering time, frequently bract tissue is visible in the center of the flower, which has only rarely been seen in Falma.

In the following description color references are made to The Royal Horticultural Society Colour Chart. The actual color of the ray florets of Light Falma is not represented in The R.H.S. Colour Chart, and the values given are those believed closest to the actual color of the ray florets. Color values were determined on plant material grown as a single stem spray cut mum in Salinas, Calif., on Jun. 20, 1990.

Classification:

*Botanical.*—*Dendranthema grandiflora* cv. Light Falma.

*Commercial.*—Flat decorative spray cut mum.

INFLORESCENCE

A. Capitulum:

*Form.*—Flat.

*Type.*—Decorative.

*Diameter across face.*—60 to 70 mm when fully opened.

B. Corolla of ray florets:

*Color (general tonality from a distance of three meters).*—Light orange.

*Color (upper surface).*—Base 12A, overlaid with 169C.

*Color (under surface).*—Closest to 12A.

*Shape.*—Longitudinally straight. Cross-section concave, slightly ribbed.

C. Corolla of disc florets:

*Color (mature).*—17B.

*Color (immature).*—144C.

D. Reproductive organs:

*Androecium.*—Present on disc florets only; very few disc florets, 1 to 6, barely visible in the mature flower; no pollen.

*Gynoecium.*—Present on both ray and disc florets.

PLANT

A. General appearance:

*Height.*—102 to 117 cm when grown in Bogota, Colombia as a single stem cut mum with 14 long days after planting rooted cuttings prior to start of short days, with no growth regulator applications.

B. Foliage:

*Color (upper surface).*—147A.

*Color (under surface).*—147B.

*Shape.*—Lobed and slightly serrated.

I claim:

1. A new and distinct Chrysanthemum plant named Light Falma, as described and illustrated.

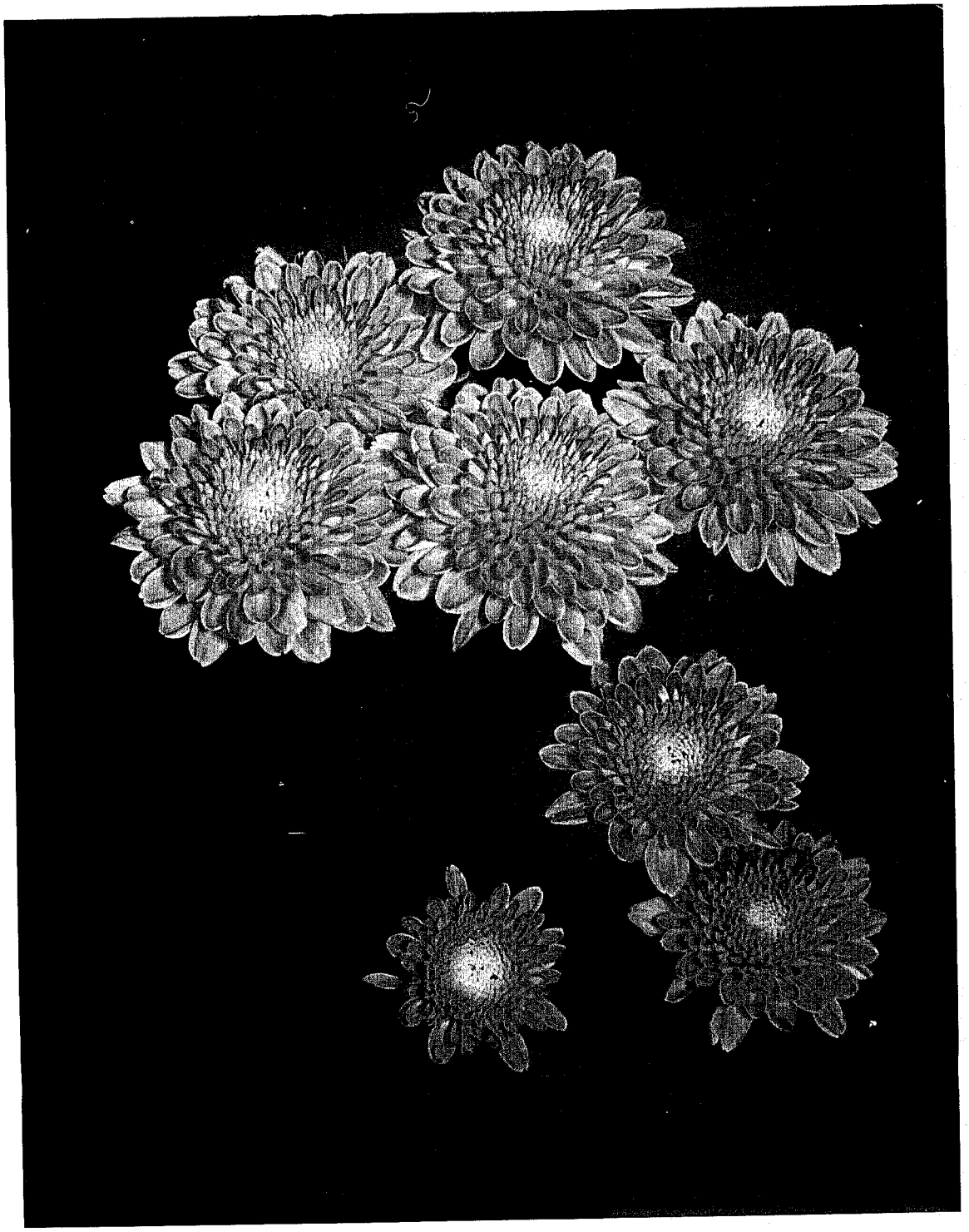

* * * * *